United States Patent
Salem et al.

(10) Patent No.: US 11,666,584 B2
(45) Date of Patent: Jun. 6, 2023

(54) STEROIDAL HORMONES FOR THE TREATMENT AND PREVENTION OF WAVE BURST ARRHYTHMIA

(71) Applicants: ASSISTANCE PUBLIQUE—HOPITAUX DE PARIS, Paris (FR); INSTITUT NATIONAL DE LA SANTÉ ET DE LA RECHERCHE MÉDICALE (INSERM), Paris (FR); SORBONNE UNIVERSITÉ, Paris (FR)

(72) Inventors: Joe-Elie Salem, Paris (FR); Christian Funck-Brentano, Paris (FR); Anne Bachelot, Paris (FR); Xavier Waintraub, Paris (FR)

(73) Assignees: ASSISTANCE PUBLIQUE—HOPITAUX DE PARIS, Paris (FR); INSTITUT NATIONAL DE LA SANTÉ ET DE LA RECHERCHE MEDICALE (INSERM), Paris (FR); SORBONNE UNIVERSITÉ, Paris (FR)

(*) Notice: Subject to any disclaimer, the term of this patent is extended or adjusted under 35 U.S.C. 154(b) by 867 days.

(21) Appl. No.: 16/094,560

(22) PCT Filed: Apr. 18, 2017

(86) PCT No.: PCT/EP2017/059097
§ 371 (c)(1),
(2) Date: Jul. 22, 2020

(87) PCT Pub. No.: WO2017/182421
PCT Pub. Date: Oct. 26, 2017

(65) Prior Publication Data
US 2020/0352960 A1   Nov. 12, 2020

(30) Foreign Application Priority Data

Apr. 19, 2016 (FR) ................................. 1653468

(51) Int. Cl.
*A61K 31/567*   (2006.01)
*A61P 9/12*   (2006.01)
(Continued)

(52) U.S. Cl.
CPC .......... *A61K 31/567* (2013.01); *A61K 9/0019* (2013.01); *A61K 9/0053* (2013.01);
(Continued)

(58) Field of Classification Search
CPC .. A61K 31/567; A61K 9/0019; A61K 9/0053; A61K 31/565; A61K 31/5685
See application file for complete search history.

(56) References Cited

U.S. PATENT DOCUMENTS

2005/0233970 A1* 10/2005 Garnick ................. A61K 31/56
514/15.6
2006/0079492 A1* 4/2006 Ahlem ................... A61P 17/00
514/178

OTHER PUBLICATIONS

International Search Report and Written Opinion dated Jul. 7, 2017 for corresponding PCT Application No. PCT/EP2017/059097.
(Continued)

*Primary Examiner* — San Ming R Hui
(74) *Attorney, Agent, or Firm* — Polsinelli PC

(57) ABSTRACT

The invention relates to a new method for the prevention and treatment of wave burst arrhythmia by administering a gestagen having an androgenic effect.

16 Claims, 4 Drawing Sheets

|  | No hormones | Levonorgestrel | Desogestrel | Gestodene | Drospirenone | P value |
|---|---|---|---|---|---|---|
| Number | 207 | 137 | 41 | 51 | 62 |  |
| Age (years) | 25.7 [21;41.7]*,$ | 23 [21; 28.5]$ | 22.8 [20.7;25.2] | 23 [21; 24.6] | 22.3 [20.7;24.7]* | <0.001 |
| Kalemia | 4.05±0.27 | 3.99±0.25 | 4±0.28 | 3.94±0.25 | 4.01±0.28 | 0.07 |
| Concentration of sotalol H3 (ng/ml) | 422 [340; 564] | 384 [257; 491] | 441 [282; 585] | 414[299;538] | 413 [341; 515] | 0.06 |
| QTcF de base (msec) | 393.8±16.9 | 392±14.2 | 390±12.1 | 393.7±14.3 | 394.7±15.2 | ns |
| RR basis (msec) | 902±104* | 882±114 | 884±98 | 869±98 | 857±100* | 0.04 |
| TAmp basis (µV) | 436±129 | 441±121 | 468±99* | 397±103* | 417±113 | 0.04 |
| TpTe basis (msec) | 66 [61; 72] | 66 [62; 71] | 63 [59.5; 67.5] | 67 [63; 71] | 65 [62; 68.3] | 0.08 |
| Notching basis (%) | 0% | 0% | 0% | 0% | 0% | ns |
| ΔQTcF (msec) | 24.6±12.5* | 24.2±13.7** | 27±12.7 | 28.1±13.2 | 31.2±12.6*,** | 0.003 |
| ΔQTcF (%) | 6.2±3.2* | 6.2±3.5** | 6.9±3.2 | 7.1±3.4 | 7.9±3.1*,** | 0.003 |
| ΔTAmp (%) | 15.7[5.8; 27.4] | 19.8[1.7; 27.5] | 18[9.2; 25.3] | 22[13.3;31.5] | 20[10.7; 29] | 0.09 |
| ΔTpTe (%) | 12.7[6.4; 24.9] | 11.7[5.9; 21.5] | 12.3[2.6; 20] | 16.3[7; 23.1] | 15.5[9; 31] | 0.1 |
| ΔRR (%) | 19.3±11.5 | 18.5±10.7 | 16.8±9.8 | 17.8±9.5 | 18.8±12.1 | ns |
| PC1 (marker of IKr inhibition) | 0.09[-0.58; 1.1]* | 0.22[-0.54; 1.2] | 0.27[-0.47; 1.2] | 0.52[-0.03;1.4] | 0.56[-0.13; 1.5]* | 0.03 |
| H3 Notching (%) | 13.4% | 16.4% | 7.3 % | 23.5% | 25.8% | 0.002 |

(51) Int. Cl.
*A61K 9/00* (2006.01)
*A61K 31/565* (2006.01)
*A61K 31/5685* (2006.01)

(52) U.S. Cl.
CPC ........ *A61K 31/565* (2013.01); *A61K 31/5685* (2013.01); *A61P 9/12* (2018.01)

(56) References Cited

OTHER PUBLICATIONS

Sedlak, T. et al., "Oral Contraceptive Use and the ECG: Evidence of an Adverse QT Effect on Corrected QT Interval," Cardiac Safety, A.N.E., vol. 18, No. 4, 2013, pp. 389-398.
Charbit, B. et al., "Effects of Testosterone on Ventricular Repolarization in Hypogonadic Men," The American Journal of Cardiology, vol. 103, 2009, pp. 887-890.
Chabbert-Buffet, N., "Contraception: evolution des progestatife," MCED, vol. 65, 2013, pp. 24-29.
Gayard, M., "Influence de la testosterone sur les parametres electrocardiografiques des hommes et des femmes," Universite de Montreal, 2013, pp. 1-103.
Halimi, S., "Le <<Dead-in-bed>> syndrome, ou la <<mort subite dans son lit>> du jeune diabetique de type 1: rare, ou meconnu?," Medicine des Maladies Metaboliques, vol. 7, No. 2, 2013, pp. 1-8.
Odening, K. et al., "Estradiol promotes sudden cardiac death in transgenic long QT type 2 rabbits while progesterone is protective," Heart Rhythm Society, vol. 9, No. 5, 2012, pp. 823-832.
Seth R. et al., "Long QT Syndrome and Pregnancy," Journal of the American College of Cardiology, vol. 49, No. 10, 2007, pp. 1092-1098.
Rodriguez, I. et al., "Drug-Induced QT Prolongation in Women During the Menstrual Cycle," Clinical Investigation—American Medical Association, vol. 285, No. 10, 2001, pp. 1322-1326.
Kurokawa, J. et al., "Pathophysiological and Pharmacological Research in Cardiology," Bio-Informational Pharmacology Bulletin, vol. 36, No. 1, 2013, pp. 8-12.
Laurent, M., "Progestatife et Anti-Androgenes," Extrait des Mises a jour en Gynecologie et Obstetrique, Paris, 1996, pp. 1-38.
Benoit, P. et al., "Prise en charge des torsades de pointe," 2009, pp. 1-7.
Schwartz, P. et al., "Predicting the Unpredictable. Drug-Induced QT Prolongation and Torsades de Pointes," Journal of the American College of Cardiology, vol. 67, No. 13, 2016, pp. 1639-1650.

* cited by examiner

|  | No hormones | Levonorgestrel | Desogestrel | Gestodene | Drospirenone | P value |
|---|---|---|---|---|---|---|
| Number | 207 | 137 | 41 | 51 | 62 |  |
| Age (years) | 25.7 [21;41.7] *,§ | 23 [21; 26.5]§ | 22.8 [20.7;25.2] | 23 [21; 24.6] | 22.3 [20.7; 24.7]* | <0.001 |
| Kalemia | 4.05±0.27 | 3.99±0.28 | 4±0,28 | 3.94±0,25 | 4.01±0.28 | 0.07 |
| Concentration of sotalol H3 (ng/ml) | 422 [340; 564] | 384 [287; 491] | 441 [282; 565] | 414 [299;538] | 413 [341; 515] | 0.06 |
| QTcF de base (msec) | 393.8±16.9 | 392±14.2 | 390±12.1 | 393.7±14.3 | 394.7±15.2 | ns |
| RR basis (msec) | 902±104* | 882±114 | 884±98 | 889±96 | 857±100* | 0.04 |
| TAmp basis (µV) | 436±129 | 441±121 | 468±99# | 397±103# | 417±113 | 0.04 |
| TpTe basis (msec) | 66 [61; 72] | 66 [62; 71] | 63 [59.5; 67.5] | 67 [63; 71] | 65 [62; 68.3] | 0.06 |
| Notching basis (%) | 0% | 0% | 0% | 0% | 0% | ns |
| ΔQTcF (msec) | 24.6±12.5* | 24.2±13.7*** | 27±12.7 | 28.1±13.2 | 31.2±12.6*,** | 0.003 |
| ΔQTcF (%) | 6.2±3.2* | 6.2±3.5** | 6.9±3.2 | 7.1±3.4 | 7.9±3.1*,** | 0.003 |
| ΔTAmp (%) | 15.7[5.8; 27.4] | 19.6[1.7; 27.6] | 18[9.9; 25.9] | 22[13.3;31.5] | 20[10.7; 29] | 0.09 |
| ΔTpTe (%) | 12.7[6.4; 24.9] | 11.7[5.9; 21.8] | 12.3[2.6; 20] | 16.3[7; 23.1] | 15.5[9; 31] | 0.1 |
| ΔRR (%) | 19.3±11.5 | 16.5±10.7 | 16.8±9.8 | 17.8±9.5 | 18.6±12.1 | ns |
| PC1 (marker of IKr inhibition) | 0.09[-0.58; 1.1]* | 0.22[-0.54; 1.2] | 0.27[-0.47; 1.2] | 0.52[-0.03;1.4] | 0.56[-0.13; 1.5]* | 0.03 |
| H3 Notching (%) | 13.4% | 16.4% | 7.3 % | 23.5% | 25.8% | 0.002 |

Figure 1

STEROIDAL HORMONES FOR THE TREATMENT AND PREVENTION OF WAVE BURST ARRHYTHMIA

CROSS-REFERENCE TO RELATED APPLICATIONS

This application is a national stage application (under 35 U.S.C. § 371) of PCT/EP2017/059097, filed Apr. 18, 2017, which claims benefit of French Application No. 1653468, filed Apr. 19, 2016, which are incorporated herein by reference in their entireties.

TECHNICAL FIELD

The present invention relates to the cardiology field, and more particularly to a novel method for preventing or decreasing the extent of repolarization disorders and therefore the risk of torsades de pointes after the occurrence of an endogenous or exogenous promoting or triggering factor such as the taking of a drug.

PRIOR ART

The term "torsades de pointes" refers to a particular type of ventricular tachycardia, which is an excessive arrhythmia of the heart ventricles that results in heart rate accelerations such as tachycardia (nevertheless different from ventricular fibrillation).

There are two types of torsades de pointes: torsades de pointes with long QT interval and polymorphic ventricular tachycardia with normal intercritical QT with twisted appearance.

The role of sex hormones in the modulation of QT or of QTc, which is QT corrected relative to heart rate, according to the methods known in the art, such as the methods of Fridericia or of Bazett, has been studied in depth, with results which are not always similar depending on the studies. Generally, however, estradiol is considered to prolong QTc, whereas testosterone or progesterone decrease QTc. Other endogenous factors such as hypokalemia, hypocalcemia, hypomagnesemia, congenital cardiac channels abnormalities, bradycardia and age also determine a prolonging of QTc interval.

New results reported in particular in this application appear to show, however, that the regulation is more complex, and involves other hormones such as gonadotropins (in particular FSH, follicle-stimulating hormone) or steroidal sex hormones or the ratios of steroidal sex hormones, such as the progesterone/estradiol ratio in women and the presence of testosterone in men. Moreover, other steroidal hormones, which are structurally similar (such as aldosterone which prolongs QTc), can also modulate ventricular repolarization.

It has been shown that women of childbearing age have a longer QTc interval during the follicular phase including their menstrual period compared to the luteal phase. This prolonging QTc is currently attributed to a defect in progesterone production during these periods. Rodriguez et al. (JAMA. 2001 Mar. 14; 285(10):1322-6) have shown that the variation in QTc after administration of a drug that prolongs QT in women of childbearing age correlates negatively with the plasma concentration of progesterone and the progesterone/estradiol ratio. Odening et al. (Heart Rhythm, Vol 9, No 5, May 2012) have shown that estradiol promotes sudden death in transgenic rabbits with a long QT interval, whereas progesterone has a protective effect. Seth et al. (JACC Vol. 49, No. 10, 2007:1092-8) have reported that women with long QT syndrome have a reduced cardiac risk during pregnancy, but said risk increases post-partum. As a result, during pregnancy, the hormonal expression profile is deeply modified with, at the end of pregnancy, a hyperexpression of progesterone resulting in concentrations expressed up to 1000 times greater than those found before pregnancy. Moreover, during pregnancy, FSH production collapses and the concentrations become virtually undetectable. Post-partum, progesterone rapidly drops and the inhibition of FSH is gradually lifted with a return to pre-pregnancy concentrations as soon as the first month following childbirth. The inventors assume that these different hormonal variations could explain the observations reported with an increase in QTc post-partum relative to the 3rd trimester of pregnancy.

There is a large number of drugs which induce an increase in QTc, and which are therefore at risk of leading to torsades de pointes in patients, all the more since they have a predisposing endogenous risk. In the vast majority of cases, the mechanism of action of this adverse effect is the inhibition of a potassium channel involved in ventricular repolarization, called IKr, which induces a prolongation of the repolarization phase and electrocardiographically results in particular in a prolonging of the QT interval corrected with respect to heart rate (QTc).

As mentioned, in Sekarski et al. (Paediatrica, Vol. 19 No. 4 2008), the prolonging of QT thus currently constitutes the most frequent cause of restriction of use and of withdrawal of drugs from the market. Among the drugs thus withdrawn from the market, this publication cites in particular cisapride, terfenadine, droperidol or sertindole.

These phenomena are particularly observed with class III anti-arrhythmics, which as a priority block potassium channels, thus prolonging repolarization. The class III anti-arrhythmics currently on the market all have a basic structure which includes a methanesulfoaniline group (or a bioisostere thereof). Mention may thus be made of amiodarone (Cordarone®), azimilide, bretylium, clofilium, dofetilide, ibutilide (Corvert®), sematilide, sotalol (Sotalex®) and dronedarone (Multaq®).

The above publication presents, in tables 1 and 2, a certain number of drugs known to prolong QT. This publication also recalls that the "University of Arizona Center for Education and Research on Therapeutics" has established and maintains a database of these drugs that can be found on their website www.torsades.org or https://crediblemeds.org/.

The website http://www.urgences-serveur.fr/prise-en-charge-des-torsadesde,1543.html cites, for its part, a certain number of drugs associated with the development of torsades de pointes.

Those which have a direct action on potassium channels:
Anti-arrhythmics:
    Class Ia: quinidine, disopyramide
    Class III: sotalol, ibutilide, amiodarone, dofetilide
Antibiotics: Macrolides: Erythromycin, Clarithromycin
Antifungals: Ketoconazole, Itraconazole, Fluconazole
Psychotropic agents: Haloperidol, Phenothiazines, Lithium, Methadone
Tricyclic antidepressants: Imipramine, Amitriptyline
Antihistamines: Astemizole, Terfenadine
Gastrokinetic agents: Cisapride
Hypolipemic agents: probucol
Those which interfere with hepatic metabolism
Substrates: terfenadine, astemizole, carbamazepine, ciclosporin, cisapride,sertraline
Inhibitors: Erythromycin, Clarithromycin, fluconazole, itraconazole The torsade de pointes (polymorphic ventricular tachycardia) attack generally lasts a few seconds and spontaneously resolves. However, because the heart, beating at a rate of greater than 200 beats per minute, no longer has time to perform its hemodynamic function, torsades de pointes are equivalent to a cardiac arrest. The patient can therefore suffer an abrupt malaise which can be of short duration, with a sensation of loss of consciousness, or can briefly lose consciousness (of syncope type) for as long as the problem lasts. The patient will be pale during this attack. In extreme forms, the torsade de pointes attack will not reduce spontaneously and may progress to ventricular fibrillation and ultimately to death.

The treatment of a patient having had an attack of torsade de pointes essentially comprises a reloading of potassium (KCl 3-6 g/d) and of magnesium (magnesium sulfate IV: 3 g IVD then 6-12 g/24H).

It is also possible to put in place electrical pacing if required, particularly in the event of bradycardia, and transfer to cardiology intensive care units is the rule.

The taking of drugs that can prolong QT (see above) should also be stopped.

In the longer term, it will be sought to identify and correct the predisposition factors (bradycardia, hypokalemia, hypomagnesemia, underlying congenital cardiopathy).

There is a need to improve the treatment of patients having presented a torsade de pointes attack, particularly in the recurring or subintrant acute forms known as "arrhythmic storm", and also to put in place a prevention of the occurrence of these events in the longer term. An arrhytmic storm is defined as the occurrence of at least two episodes in less than 24 hours or three episodes in less than 48 hours of ventricular rhythm disorders requiring treatment with a defibrillator.

According to Halimi (Médecine des maladies Métaboliques [Medicine of metabolic diseases]—March 2013—Vol. 7—No.), "the "Dead-in-Bed" syndrome involves rare subjects with type 1 diabetes, who are very young and without any early warning sign, other than a high frequency of severe hypoglycemia. These unexplained deaths, which are up to ten times more frequent than in the paired non-diabetic population, are thought to be due to the sequence hyperinsulinism, hypoglycemia, hypokalemia, in parallel to the activation of the sympathetic system, and to a medical background predisposing to the triggering of serous rhythm and/or conduction disorders. However, severe nocturnal hypoglycemia is frequent, and only exceptionally causes such dramatic consequences. The hypoglycemia systemically causes a prolonging of the QT interval, but the amplitude of this varies according to individuals, probably due to genetic predispositions, such as in familial long QT syndromes". It therefore appears that a preventive treatment that can reduce the QT interval would potentially be positive for such patients.

Sedlak et al. (Ann Noninvasive Electrocardiol. 2013 July; 18(4):389-98) report the results of an epidemiological transverse study in order to evaluate the relationship between oral contraceptives and the QTc interval. This is a study with a low level of evidence, in particular because the groups exposed to various types of pills are very different to one another, and show numerous comorbidities. Moreover, the QTc measurements are automatic without manual verification, and are carried out on traces produced in the context of common care and not with the objective of a research determined a priori. There are a very large number of biases not taken into account in this study due to its retrospective nature, in particular such as the absence of detailed information and of taking into account the cotreatments taken by the subjects at the time of their electrocardiographic measurement.

Thus, the amplitude of the differential effects demonstrated in this study is minimal (4 ms), and at the limit of clinical relevance (as a result, for analysis of the drugs, it is considered that said drugs have no risk of inducing cardiac repolarization as long as the prolonging of the QTc is less than 5 msec) and on a basal QTc measurement (that is to say without stimulation with a QTc-increasing compound) despite very large numbers (approximately 400 000 ECGs). Moreover, Sedlak et al. do not have a group of patients taking pills with gestodene, by way of comparison.

It should also be noted that there is no demonstration of differences between the QTc lengths as a function of the type of pills in the case of cotreatment (Table 5 and discussion).

These results therefore differ from those reported in the present application which are based on a study with an absence of demographic differences as a function of the type of pill, and the submission of the patients to a standardized pharmacologic stimulus known to promote torsades de pointes. The present application shows that differences of more than 5 ms (approximately 7 ms) are observed as a function of the type of pills, added to the average 20 ms observed with sotalol, despite small numbers per group (n=50).

Moreover, it is recalled that the QTc is associated with the risk of torsades de pointes, but is not specific for drug-induced TDPs. The present application also shows that the type of pills influences a series of other associated markers, more specific for an inhibition of IKR (assumed mechanism of action of drug-induced torsades de pointes). It involves in particular a difference regarding the appearance of notches and the modification of PC1 (new more relevant composite marker of IKr inhibition).

Finally, Sedlak et al. does not in any way mention the therapeutic potential of the pills in the prevention or treatment of torsades de pointes.

Meriggiola et al. (J Clin Endocrinol Metab. 2005 April; 90(4):2005-14) describe the use of norethisterone enanthate and of testosterone. Norethisterone enanthate is not included in general formula (I) below.

SUMMARY OF THE INVENTION

The invention relates to a compound of formula (I) for use thereof in the treatment and prevention of the recurrence of torsades de pointes.

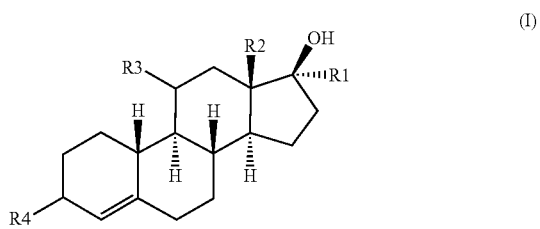

wherein
R1 is chosen from H, $CH_3$, $CH_2$—$CH_3$, CH=$CH_2$, C≡CH
R2 is chosen from $CH_3$, $CH_2$—$CH_3$, CH=$CH_2$, C≡CH
R3 is chosen from —H, —$CH_3$, =$CH_2$ (the bond between the carbon of the ring and R3 then being a double bond), ≡CH (the bond between the carbon of the ring and R3 then being a triple bond)

R4 is chosen from —H, —OH and =O (the bond between the carbon of the ring and R4 then being a double bond).

In one preferred embodiment,

R1 is C≡CH

R2 is chosen from CH$_3$, CH$_2$—CH$_3$

R3 is chosen from —H, =CH$_2$ (the bond between the carbon of the ring and R3 being a double bond)

R4 is chosen from —H and =O (the bond between the carbon of the ring and R4 being a double bond).

In one preferred embodiment, the compound of formula (I) is levonorgestrel of formula (II):

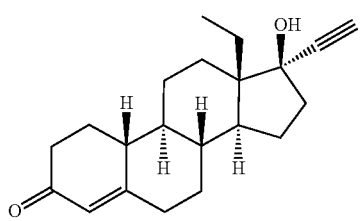

(II)

In this embodiment, R1 is C≡CH, R2 is CH$_2$—CH$_3$, —R3 is —H and —R4 is =O.

It should be noted that levonorgestrel can be used pure or substantially pure, or in a racemic mixture (norgestrel) with the non-active isomer compound.

In another embodiment, the compound of formula (I) is norethisterone of formula (III):

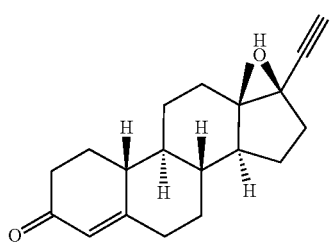

(III)

In this embodiment, R1 is C≡CH, R2 is CH$_3$, —R3 is —H and —R4 is =O.

In another embodiment, the compound of formula (I) is desogestrel of formula (IV)

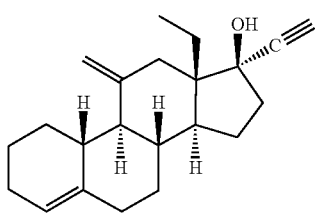

(IV)

In this embodiment, R1 is C≡CH, R2 is CH$_2$—CH$_3$, —R3 is =CH$_2$ and —R4 is —H.

In another embodiment, the compound of formula (I) is etonogestrel of formula (V) (active metabolite of desogestrel)

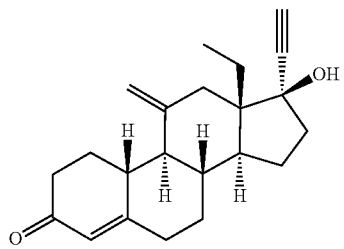

(V)

In this embodiment, R1 is C≡CH, R2 is CH$_2$—CH$_3$, —R3 is =CH$_2$ and —R4 is =O.

In the implementation of the present invention, use will preferentially be made of progestogens which provide a progestogen environment and also very preferentially have an androgenic activity. The progestogens used in the context of the present invention are therefore preferentially derived from 19-nortestosterone (nandrolone) of formula (VI), which could potentially be used in the context of the invention

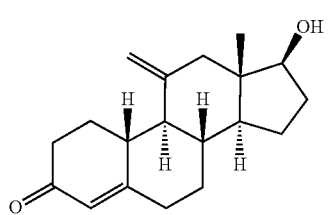

(VI)

In this embodiment, R1 is H, R2 is CH$_3$, —R3 is —H and —R4 is =O.

However, use could also be made of medroxyprogesterone (17α-hydroxy-6α-methylprogesterone), and in particular medroxyprogesterone acetate of formula (VII), in the context of the present invention

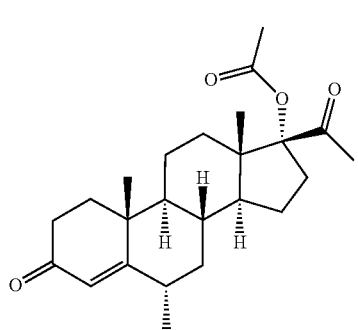

(VII)

On the other hand, the use of dienogest or norgestimate, which have a low androgenic activity, or even an anti-androgenic activity, will be avoided.

It is recalled that a progestogen is a steroidal hormone having an action similar to progesterone, which exhibits the following effects experimentally in a laboratory animal:
luteomimetic effect (Clauberg test): secretory differentiation on a uterine mucosa correctly prepared by estrogens
progestogenic effect: maintenance of gestation despite ablation of the yellow body of the ovary.

These properties are well known to those skilled in the art and can therefore be readily tested (see https://fr.wikipedia.org/wiki/Progestogen).

The androgenic activity can readily be evaluated by methods known in the art, by studying the capacity of the progestogen to bind to and to activate the androgen receptor (NR3C4).

The compound used preferably has the strongest possible antigonadotropic activity on the hypothalamic-pituitary axis. Indeed, there is a positive association between QTc and FSH (Abehsira et al., J Clin Endocrinol Metab. 2016 July; 101(7):2776-84). One of the mechanisms of action of the pills is the antigonadotropic activity (central decrease in FSH and LH) but the pills are not all equivalent in this respect. It is preferred when, for the prevention of torsade de pointes, the compound used has a strong intrinsic progestogenic androgenic activity associated with a important antigonadotropic activity (leading to a decrease in FSH).

The compound of formula (I) is therefore used for the treatment and prevention of the recurrence of torsades de pointes.

The expression "treatment and prevention of the recurrence of torsade de pointes" is intended to denote the treatment carried out after a torsade de pointes attack or during an arrhythmic storm. Thus, the compound of formula (I) will be administered to a patient within three days following the occurrence of an episode of torsade de pointes in this patient, preferably within 48 hours or 24 hours following this episode. However, the compound of formula (I) is preferably used as rapidly as possible after the episode of torsade de pointes, in the same way as the other treatments described above.

In this embodiment, the compound of formula (I) is used for treating the acute phase following the torsade de pointes, or during an episode of arrhythmic storm. The patient will therefore be treated after the latter has had an episode of torsade de pointes, for a period of less than or equal to one month, generally for a period of less than or equal to 15 days.

The compound of formula (I) will assist in reducing the inhibition of the IKr potassium channel and in reestablishing ventricular repolarization.

In this embodiment, use will be made of the compound of formula (I) at a dose of between 30 µg/day and 3 mg/day. This dose may be administered in one dose or several doses.

In another embodiment, the invention relates to a compound of formula (I), as defined above, for the primary and secondary prevention of the occurrence of episodes of torsades de pointes in a patient.

Use may also be made of medroxyprogesterone (17α-hydroxy-6α-methylprogesterone), and in particular medroxyprogesterone acetate of formula (VII) in the context of the present invention for this aspect of the invention.

The term "primary prevention" is intended to denote the fact that the patient has not presented a torsade de pointes event prior to the beginning of the treatment.

The term "secondary prevention" is intended to denote the fact that the patient has already had at least one torsade de pointes event, but that he is no longer in arrhythmic storm or that this episode occurred at least one month before the initiation of the treatment.

In this embodiment, the patient may have a predisposition to the occurrence of torsades de pointes. This is in particular the case when the patient has at least one of the following symptoms:
 long QT syndrome
 hypokalemia
 hypomagnesemia
 bradycardia
 paroxymal cardiac arrhythmia
 an underlying, in particular ischemic, cardiopathy
 hypogonadism in men
 treatment with a QT-increasing drug
 constitutive progesterone deficiency in women
 diabetes, preferentially type I diabetes.

Thus, the invention relates to a compound of general formula (I) for the use thereof for the prevention of sudden death in a diabetic patient.

The invention also relates to a composition containing a compound of general formula (I) and IGF-I (insulin-like growth factor-1) for use thereof simultaneously, separately or spread out over time, for the prevention of sudden death in a diabetic patient. IGF-I is a linear peptide of 70 amino acids consisting of four domains (B, C, A, D), domains B and A of which are similar to those of insulin, discovered and characterized in 1987.

The invention also relates to a composition containing a compound of general formula (I) and an androgen for use thereof simultaneously, separately or spread out over time, for the prevention of sudden death in a diabetic patient, the patient being male.

In the context of the invention, it is therefore possible to envision a composition containing both a compound of general formula (I) and an androgen, that can be used in particular orally. The androgen is in particular as described below.

In this embodiment, the daily amount of compound of formula (I) administered to the patient is between 30 µg and 300 µg, for a long-term treatment (that is to say a treatment for at least two months). It should be noted that compound of formula (can be not administered to the patient for a few days per period of 28 days. The amount can however be much higher (500 µg to 1 mg per day) for certain compounds of formula (I), in particular for norethisterone.

It should be noted that the compounds cited above are currently used as progestogens in the context of an oral contraception in women.

In order to maintain the periods in these patients, the latter do not take contraceptives for four to five days every 28 days.

In the context of the method for preventing torsades de pointes, it is however preferable to give the compounds mentioned above continuously, that is to say without a rest of the treatment over time.

However, it is possible to envision, if required by the needs of the patient, to interrupt the treatment for a few days (4 or 5 days) per month, every 28 days. This will maintain the periods in the patients.

Another embodiment of the invention therefore relates to a compound of general formula (I) as defined above, and also any other compound described above, for use thereof in an oral contraception scheme in a woman, said woman having a risk of presenting an episode of torsade de pointes.

For such patients, it is in fact preferable to choose an oral contraception composition containing a progestogen as mentioned above, rather than a composition with an estrogenic environment (in particular containing gestodene, norgestimate or drospirenone).

It is however understood that the prescription of contraception must take into account all of the characteristics of the patient and that the practitioner will adjust this prescription case by case.

In one preferred embodiment, the compound of general formula (I) is in a form suitable for oral administration. Such compositions already exist in the art (contraceptive pills), and the daily taking of a single pill containing an appropriate dose makes it possible to deliver the required dose, in particular in the case of a long-term treatment for preventing the occurrence of events of torsades de pointes.

The pills that exist on the market generally contain an estrogen, in addition to the compound of general formula (I) or to the progestogen described above. It is sometimes preferable to eliminate this estrogen in the context of the methods and treatments described in the present application, in order to increase the protective effect of the progestogen and compound of formula (I).

Thus, in this embodiment, the composition administered to the patient contains, as active ingredient, only the compound of general formula (I). This means that the other elements contained in the composition are excipients which have no known or listed effect on progesterone receptors, androgen receptors or estradiol receptors, or other known or listed effect in the cardiovascular field. In general, these excipients do not have a known or listed physiological effect. In particular, the composition contains no other natural or synthetic hormone having a known or listed effect on progesterone receptors, androgen receptors or estradiol receptors.

In another embodiment, the composition can contain an estrogen (such as ethinyl estradiol, estradiol, or estradiol valerate). In this embodiment, the unit doses of the compositions generally contain about 15-40 μg of estrogen, whereas they contain between 50 and 200 μg of compound of formula (I). It is even possible to envision pills containing 500 μg to 1 mg of norethisterone with approximately 35 μg of estrogen (ethinyl estradiol).

In the context of the treatments described in the present invention, use may also be made of compositions in which the estrogen doses are lower than those mentioned above.

In the context of the treatment of an event, in the case in particular of arrhythmic storm, it is possible to give pills that already exist, such as Norlevo®, each unit dose of which contains 1.5 mg of levonorgestrel, two pills of which can be taken in one or two intakes.

In general, the composition according to the invention can be in any other form known in the art. In particular, it can be in the form of gel capsules, of tablets (film-coated or non-film-coated), of pills or of lozenges. In another embodiment, it is in the form of a liquid composition, such as a syrup.

In the case where the composition is in a solid form, use may be made of any excipient known in the art, such as talc (E553b), microcrystalline cellulose, lactose, starch (in particular corn starch), magnesium stearate (E572), stearic acid (E570) or microcrystalline cellulose. When the composition is in the form of a film-coated tablet, said film-coating may be formed of any substance known in the art, such as hypromellose (E464), ethylcellulose, macrogol, talc (E553b), titanium dioxide (E171) or iron oxide (E172).

The compositions could optionally be slow release, even though such compositions are not preferred, due to the need for rapid delivery of the active principle in the event of arrhythmic storm, and to the (contraceptive) second effect in the event of long-term treatment.

In another embodiment, the compound of formula (I) is in a form suitable for injectable (in particular intravenous) administration. This case is particularly suitable during the treatment of an episode of torsades de pointes, in the event of a recent event or of arrhythmic storm.

In other embodiments, the compounds can be delivered by subcutaneous implant. Such implants are used in contraception, and contain the compounds mentioned above. Once the implant is put in place, the compound diffuses directly in the blood. The implants currently on the market (Nexplanon®) generally contain sufficient hormone to be effective for three years.

The compounds mentioned above can also be delivered via impregnated IUDs, in particular the Mirena® IUD, inserted into the uterine cavity where it delivers levonorgestrel for five years.

The compounds can also be delivered via an impregnated vaginal ring, which is replaced every three weeks.

The compounds described above can be delivered via topical compositions (ointments or creams, in particular vaginal ointments or creams).

It is also possible to envision these compounds being delivered by means of a transdermal patch.

In general, it is highly preferred for the patient to be female. However, the compound of formula (I) can also be used in men, in particular and preferably when an androgen is administered in combination with the compound of formula (I).

The invention thus relates to a composition containing a compound of formula (I) and an androgen (a steroidal hormonal compound which activates the NR3C4 receptor) for use thereof simultaneously, separately or spread out over time, for the treatment or prevention of torsades de pointes.

In one preferred embodiment, said androgen is chosen from the group consisting of testosterone, dehydroepiandrosterone, Δ4-androstenedione, androsterone and dihydrotestosterone.

Such a combination therapy can be used in men and women.

The present invention also covers the use of a compound of general formula (I) for the preparation of a drug intended for the treatment of torsades de pointes.

The present invention also covers the use of a compound of general formula (I) for the preparation of a drug intended for the (primary or secondary) prevention of the occurrence of episodes of torsades de pointes or of the occurrence of repolarization disorders suggestive of a high risk of torsades de pointes.

The present invention also relates to the use of a compound of general formula (I) for the preparation of an oral contraceptive intended for women who have a risk of occurrence of torsades de pointes or of occurrence of repolarization disorders suggestive of a high risk of torsades de pointes.

The present invention also relates to the use of a compound of general formula (I) for the preparation of a drug intended for reducing QT in a patient.

The present invention also covers a method for treating a patient having had an episode of a torsade de pointes, or of arrhythmic storm, comprising the administration of an appropriate amount of a compound of formula (I) to the patient.

The present invention also covers a method for (primary or secondary) prevention of the occurrence of episodes of torsades de pointes in a patient or of the occurrence of repolarization disorders suggestive of a high risk of torsades de pointes, comprising the administration of an appropriate quantity of a compound of formula (I) to the patient.

The present invention also covers a method for reducing the QT in a patient, comprising the administration of an appropriate amount of a compound of formula (I) to the patient.

More specifically, the invention covers the administration, to a patient requiring it, of a compound of formula (I) or more specifically described above, in an amount sufficient for treating or preventing one or more episode(s) of torsades de pointes, and/or decreasing the QTc in this patient. This compound can be administered alone or with another compound (in particular as described as above, IGF-I or with androgenic property), which is used simultaneously, sequentially or spread out over time. The administration is carried out as described above, and in particular orally or subcutaneously.

BRIEF DESCRIPTION OF THE FIGURES

FIG. 1: characteristics of the patients having received sotalol, and of their method of contraception. H3 represents the value three hours after administration of sotalol.

Statistics: ns represents p>0.1. Various tests (Chi$^2$ test with trend, one-way ANOVA with Tukey or Kruskal-Wallis post-test with Dunn's post-test) were used. The quantitative data are presented as a mean±standard error or median with interquartile range.

*(no hormones vs drospirenone), **(levonorgestrel vs drospirenone), # (desogestrel vs gestodene), § (levonorgestrel vs no hormones), ‡ (gestodene vs no hormone).

The PC1 value is obtained by analysis by main components of the variables ΔQTc (%), ΔTpTe (%) and ΔTAmp (%) and quantitatively reflects the IKr inhibition obtained three hours after taking sotalol.

Figure 2:
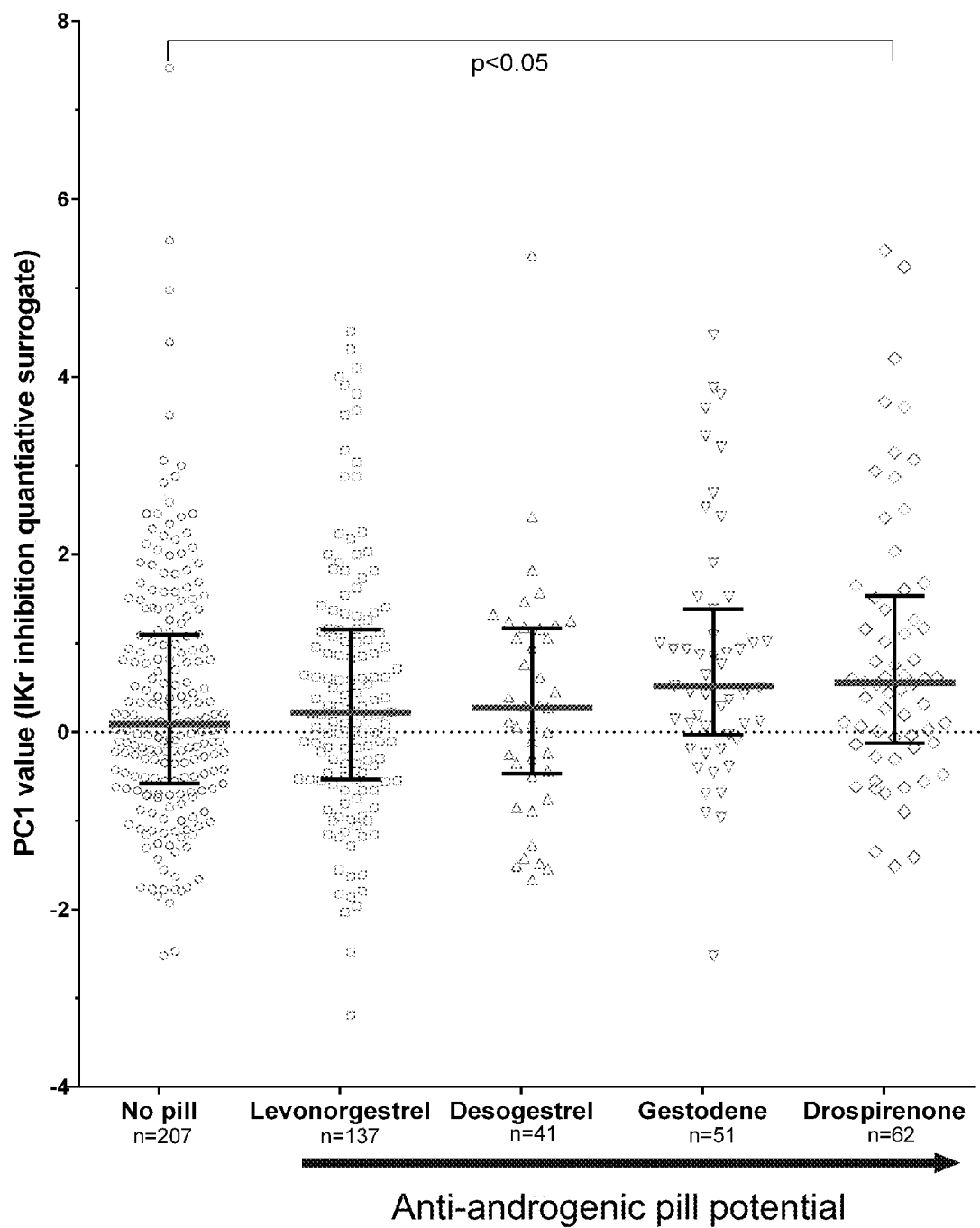

FIG. 2: PC1 value three hours after administration of 80 mg of sotalol as a function of the pill type. The statistics (significant values) were obtained by means of a Kruskal-Wallis test with Dunn's post test. Significance with threshold: p<0.05.

Figure 3:
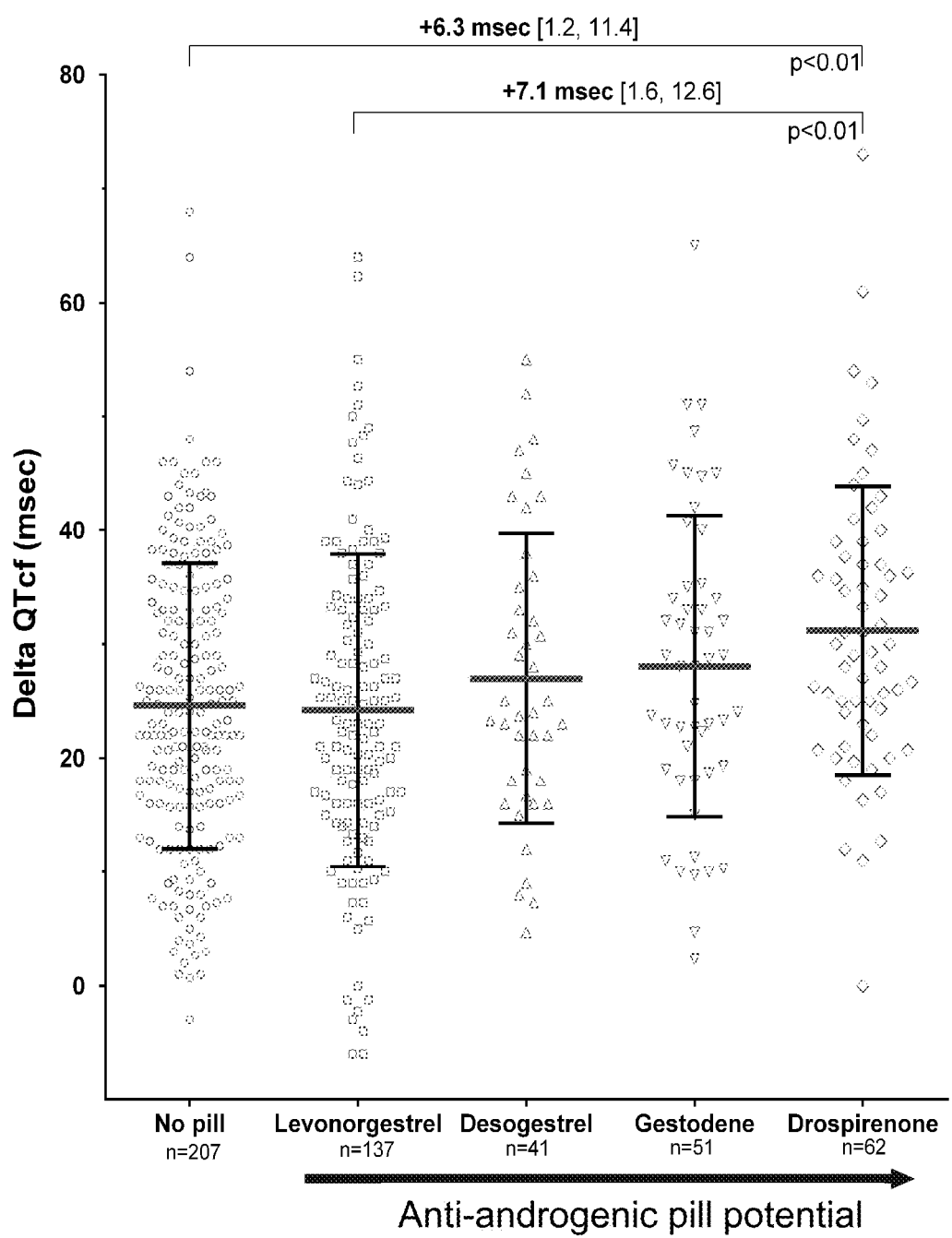

FIG. 3: Value of the difference in QTc (ms) three hours after administration of 80 ms of sotalol as a function of the pill type. The statistics (significant values) were obtained by ANOVA with Tukey post-test, p<0.01.

Figure 4:
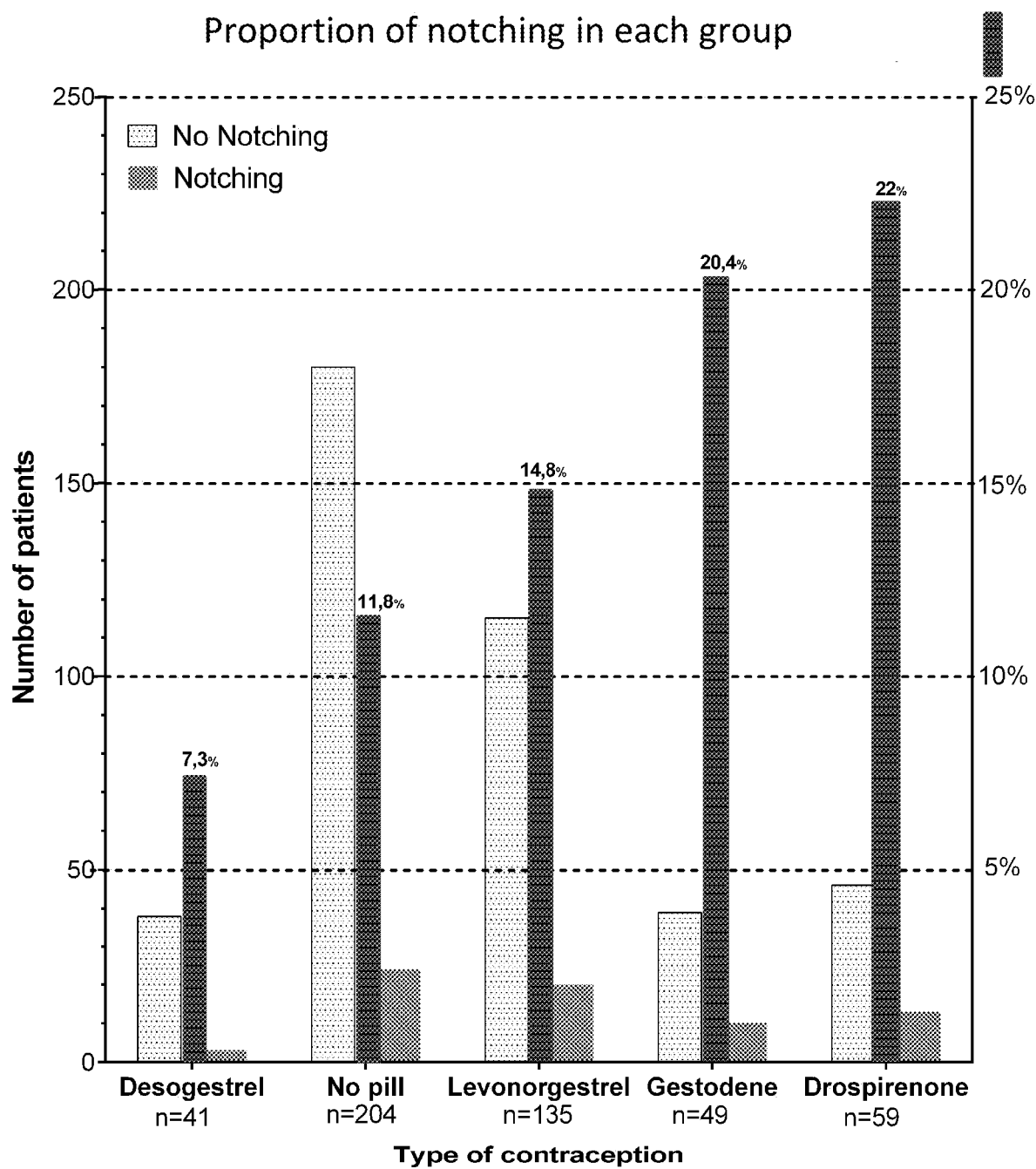

FIG. 4: number and proportion of patients with a double T-wave peak induced by sotalol as a function of the type of contraception.

EXAMPLES

Example 1—Development of a Marker Representative of Inhibition of the IKr Potassium Channel Results obtained on a cohort of 995 volunteers in good health, from 18 to 60 years old, of European or North African origin, were used for the development of a marker representative of inhibition of the IKr potassium channel.

The results were obtained on an exploration cohort, having served to identify the marker described below, and a replication cohort having served to verify the results obtained on the exploration cohort.

Briefly, the electrocardiogram (ECG) of the patients (each one in triplicate, for 10 seconds) was recorded after 10 minutes at rest lying on their back. A single oral dose of 80 mg of sotalol was then given to the patients and the ECG monitoring was continued. Three hours after the sotalol had been taken, the ECG was again recorded (in triplicate) after the subjects had remained lying on their back for 10 minutes.

ECG Analysis

The increase in the QT by sotalol represents the equivalent of the congenital iatrogenic form of long QT syndrome LQT2; the appearance of the conventional differences between the basal trace and the trace three hours after taking sotalol was verified on the ECG.

The QTcF (QT corrected using Fridericia's formula), TpTe (interval between the first peak and the end of the T wave), TAmp (amplitude of the first peak of the T wave) and the presence of double peaks in the T wave (called notches) were quantified. The Fridericia correction (QTcF) was used to correct the QT with respect to the heart rate, in accordance with the ICH guidelines E14.

The analysis of the ECG data was carried out with the CARDIABASE software (Group Banook, Nancy, France).

TpTe was measured using the tangent method, in triplicate, on a representative heart beat (averaged representation of an ECG of 10 seconds) on the V3, V4 and V5 derivations. In the event of a double peak of the T wave (notch), the peak taken into consideration was the first peak, even if the amplitude of the T wave was smaller for this peak. The average value obtained was retained. In the event of it being impossible to measure TpTe on V3, V4 or V5, the measurement was instead carried out on V2 (for V3), or V6 (for V4/V5).

In order to measure TAmp, positioning was on the site of the maximum amplitude of the first peak of the T wave on a representative beat (averaged representation of an ECG of 10 seconds) on the DII, V2 and V3 leads. The average of the TAmp values resulting from these three leads, and measured on three different ECGs of 10 seconds (in triplicate), was calculated and retained. If it was not possible to measure a TAmp on one of these leads (in particular because of a low value (<0.1 mV)), the V4 lead was used.

QTcF was measured using the tangent method on the DII lead for three consecutive beats and the average value of an evaluation in triplicate was retained.

It was possible to verify that the measurements remained consistent and reproducible between the evaluators.

For these parameters, the difference between the value obtained at H3 and the basal value was measured. This difference was expressed as percentage relative to the basal value, and the calculations were carried out such that the value calculated is positive.

The following calculations were therefore carried out:

$$\Delta QTcF\ (\%) = (QTcF\ at\ H3 - QTcF\ basal)/(QTcF\ basal) \times 100$$

$$\Delta TpTe\ (\%) = (TpTe\ at\ H3 - TpTe\ basal)/(TpTe\ basal) \times 100$$

$$\Delta TAmp\ (\%) = (TAmp\ basal - TAmp\ at\ H3)/(TAmp\ basal) \times 100$$

In order to evaluate the double peaks (notches), all the ECGs were evaluated independently by two investigators. The patients were described as notchers or non-notchers, in the event of agreements between the two investigators. In the event of disagreement in the evaluation, the subjects were not included in these groups (only ten subjects in the evaluation cohort and eight subjects in the replication cohort could thus not be classified).

Principal Component Analysis

A principal component analysis was carried out on the calculated values ΔQTcF, ΔTpTe and ΔTAmp, which made it possible to generate three non-correlated alternative markers PC1, PC2 and PC3, taking better account of the information carried by the three initial correlated values. The statistical analyses were carried out with the R software (https://www.r-project.org/). Principal component analysis (PCA) is a method which makes it possible to convert correlated variables into new variables which are not correlated with one another.

Results

Sotalol-Induced Changes in the Electrocardiogram

The changes observed in the electrocardiogram three hours after administration of sotalol suggest an inhibition of the IKr channel, with results and observations similar in the exploration and replication cohorts, regardless of the qualitative or quantitative parameters evaluated.

In agreement with previous studies, sotalol also induces absolute and relative changes in the duration of QTcF (21.4±14 ms and 5.5±3.5% respectively).

Typical changes in the shape of the T wave were also observed, with an increase in TpTe (14.2±15.6 vs 15.9±20.5%, p=ns (not significant)) and a decrease in TAmp (13.6±15.7 vs 12.8±15.3%, p=ns) respectively between the exploration and replication cohorts.

However, a large inter-subject variability was observed in all the changes observed. The variations in TpTe, TAmp and QTcF between H3 and the basal level exhibit an autocorrelation in the same proportion between the two cohorts.

Finally, 40 (8%) or 51 (10%) subjects exhibited a double peak (notch) in each of the two cohorts. They were almost exclusively women, and these patients had a higher ΔTpTe, ΔQTcF and ΔTAmp than those observed for the non-notchers (patients without double peak).

Principal Component Analysis

The principal component analysis made it possible to generate three new quantitative values, linked to the sotalol-induced modifications of ventricular repolarization.

The first component (PC1) explaining approximately 65-67% of the phenotypic variance reflects the typical modifications after inhibition of the IKr channel, that is to say the increase in TpTe and QTcF and the decrease in TAmp (Table 1).

The PC1 variable under consideration is the variable which correlates best with each of ΔQTc, ΔTAmp and ΔTpTe. This signifies that the correlation coefficient that can be calculated for PC1 with each of ΔQTc, ΔTAmp and ΔTpTe is greater (in absolute value) than the correlation coefficient that is calculated for the other principal components of PC2 and PC3 for ΔQTc, ΔTAmp or ΔTpTe in question. Table 1 of the examples clearly shows that the absolute value of the correlation coefficient of PC1 is greater than the absolute value of the correlation coefficient of PC2 and PC3, calculated for each of ΔQTc, ΔTAmp and ΔTpTe.

Depending on how the principal component analysis is carried out, PC1 can correlate positively or negatively with ΔQTc, ΔTAmp and ΔTpTe described above. The PC1 value is very clearly associated with the appearance of ECG sign determining an inhibition of IKr, and presumed to be associated with an increased risk of episode of torsade de pointes with long QT.

In the context of the calculation carried out in this study which made it possible to demonstrate the PC1 marker, PC1 correlates negatively with ΔQTc, ΔTAmp and ΔTpTe.

Consequently, the increase in these values leads to a decrease in PC1.

A significant decrease in the PC1 value ($p<10^{-4}$) was observed in the patients exhibiting a double peak (notchers) compared with the patients not exhibiting this double peak (non-notchers) in one or other of the exploration (−2.5±1.5 vs 0.3±1.1) or replication (−2.3±1.8 vs 0.3±1.1) cohorts.

The PC1 value is therefore a quantitative alternative value of the inhibition of IKr.

The other principal components (PC2 and PC3) explained, respectively, approximately 19-21% and 14% of the phenotypic variance.

TABLE 1

Correlations (r) between ΔTAmp, ΔTpTe, ΔQTcF and the principal components in the exploration cohort (n = 489, upper part of the table) or the replication cohort (n = 495, lower part of the table)

| Correlation(r) | ΔTAmp | ΔTpTe | ΔQTcF | PC1 | PC2 | PC3 |
|---|---|---|---|---|---|---|
| ΔTAmp | 1 | 0.59 | 0.40 | −0.83 | 0.36 | −0.43 |
| ΔTpTe | 0.58 | 1 | 0.45 | −0.85 | 0.23 | 0.47 |
| ΔQTcF | 0.47 | 0.46 | 1 | −0.73 | −0.68 | −0.06 |
| PC1 | −0.84 | −0.84 | −0.78 | 1 | 0 | 0 |
| PC2 | 0.28 | 0.3 | −.063 | 0 | 1 | 0 |
| PC3 | −0.46 | 0.45 | 0.01 | 0 | 0 | 1 |

It is clearly observed that PC1 correlates in the same sense with ΔTAmp, ΔTpTe and ΔQTcF (correlated negatively in this example), which is not the case for PC2 or PC3.

It is also observed that the absolute value of the correlation coefficients of PC1 with ΔTAmp, ΔTpTe and ΔQTcF is greater than that of PC2 or PC3 with these values.

Conclusion

As expected, an increase in TpTe and QTcF and a decrease in TAmp were observed between the basal level and three hours after taking sotalol.

The new PC1 value obtained by principal component analysis of ΔQTcF, ΔTpTe and ΔTAmp explains most of the total variance of the "A" data (ΔQTcF, ΔTpTe and ΔTAmp) and is thus associated with the common mechanism of increase in QTcF and TpTe, associated with the decrease in TAmp.

Consequently, PC1 is a quantitative and integrative marker for drug-induced IKr inhibition.

Example 2—Levonorgestrel and Desogestrel have a Rather Protective Action on the Inhibition of the IKr Potassium Channel Population The study was carried out on 615 women in good health, of European or North African type, between the ages of 18 and 60, with a QTcF<450 ms, and no known disease or chronic, or chronic treatment, except a contraception, and without any family history of congenital long QT syndrome, arrhythmia, or sudden death.

Measurement and Calculation of the Various QTcF, TAmp and TpTe Data

The QTcF, TAmp and TpTe were measured according to the same protocol as for example 1, before and three hours after administration of a single oral dose of sotalol at 80 mg.

The ΔQTcF, ΔTpTe and ΔTAmp were also calculated.

Principal Component Analysis

A principal component analysis was carried out on ΔQTcF, ΔTpTe and ΔTAmp (XLStat software, Addinsoft) in order to generate three new decorrelated values PC1, PC2 and PC3.

Results

The PC1 variable thus obtained (of which the absolute value of the correlation coefficients with ΔTAmp, ΔTpTe, and ΔQTcF is greater than that of the correlation coefficients for PC2 or PC3 with these values) explains 63% of the phenotypic variance observed (characterized by the increase in QTcF and TpTe and the decrease in TAmp). In this embodiment, PC1 correlates positively in the same sense as ΔQTcF, ΔTpTe and ΔTAmp, that is to say that it increases when these values increase (Table 2).

TABLE 2

Correlation between the variables and the factors
obtained after PCA, and contribution of each of
these factors to the total variance (n = 498).

|  | PC1 | PC2 | PC3 |
|---|---|---|---|
| ΔQTcF (%) | 0.71 | 0.71 | −0.06 |
| ΔTpTe (%) | 0.85 | −0.24 | 0.48 |
| ΔTAmp (%) | 0.83 | −0.36 | −0.44 |
| Contribution to the total variance | 63.2% | 22.7% | 14.1% |

FIG. 1 shows the various characteristics of the patients having received sotalol, and also the contraceptive hormone.

The following are observed:

The basal levels of QTcF, and the sotalol concentrations in the plasma three hours after administration, and also the kalemia, were not different between the subgroups as a function of the type of contraception.

The increase in QTcF for the patients taking drospirenone was greater than that observed for the patients without hormonal contraception (6.6±2.6 msec) or taking levonorgestrel (7.0±2.7 msec) (FIG. 3).

The patients taking drospirenone and gestodene exhibited a greater incidence (p<0.01) of double peaks (notches) three hours after administration of Sotalol (25.8% and 23.5% respectively) than the patients taking desogestrel (7.3%), levonorgestrel (16.4%) or without hormonal contraception (13.4%) (FIG. 4).

The value of PC1 was significantly higher in the drospirenone group than in the group of patients without oral contraception (respectively 0.56 [−0.13; 1.5] and 0.09 [−0.58; 1.1], p<0.05) (FIG. 2).

The value of PC1 was more moderate in the desogestrel group and levonorgestrel group (respectively 0.27 [−0.47; 1.2] and 0.22 [−0.54; 1.2]) (FIG. 2).

It is therefore seen that not all the methods of oral contraception are identical with regard to the risks of inhibition of the IKr channel induced by taking drugs.

Drospirenone exhibits the greatest risk of drug-induced IKr inhibition, while levonorgestrel, and desogestrel, appear to be neutral, levonorgestrel instead being protective with regard to the increase in QT and desogestrel instead being protective with regard to the appearance of a double peak (notch) of the T wave.

The inventors put forward the hypothesis that this is due to both the progestogenic and the androgenic effect of these two hormones, compared with drospirenone, which does not have an androgenic effect (Table 3).

If the doses of estrogens (ethinyl estradiol) administered at the same time as these progestogens are decreased or eliminated, the protective effect of these progestogens would be all the more marked.

TABLE 3

Characteristics of the various oral pills for hormonal contraception

|  | Levonorgestrel | Desogestrel | Gestodene | Drospirenone |
|---|---|---|---|---|
| Number of patients | 137 | 41 | 51 | 62 |
| Concomitant use of EE (%) | 99 | 78 | 100 | 100 |
| EE dose min/max* (μg/day) | 20-35 | 20-30 | 15-35 | 20-30 |
| PG dose min/max* (μg/day) | 30-175 | 75-150 | 60-75 | 3000 |
| Pill generation | $2^{nd}$ | $3^{rd}$ |  | $4^{th}$ |
| Progestogenic activity | High | High |  | Intermediate |
| Androgenicity | High | Intermediate/variable |  | Anti-androgenic |

Abbreviations: EE: ethinyl estradiol, PG: progestogen,
*in the event of concomitant use of EE, except on the days with placebo or without pills Example 3—Treatment of a Torsade De Pointes by Administration of Testosterone Peripheral hypogonadism was identified in a man suffering from ischemic cardiopathy and from Erdheim-Chester disease with arrhythmic storm on torsades de pointes with long QT and notching (double peak (notch) of the T wave) promoted by iatrogenesis and bradycardia with more than seven episodes in less than one week.

Testosterone (Androtardyl, testosterone enantate 250 mg/ml) was administered to the patient in amounts which made it possible to maintain a testosterone level making it possible to correct his hypogonadism, the bradycardia was corrected and an implantable defibrillator was implanted as secondary prevention.

Following the introduction of testosterone, the circulating concentration of bioavailable testosterone and his repolarization became normalized.

Three months following the introduction of testosterone, the monitoring of the defibrillator confirmed the absence of recurrence of torsades de pointes despite the reintroduction of QTc-prolonging drug (Vemurafenob) which the patient required for his background health (Erdheim-Chester).

This clinical case is in favor of the effectiveness of a hormonal modulation for the treatment and prevention of torsades de pointes.

Conclusion

Example 3 is the first demonstration that testosterone, beyond its discussed effect on QTc, is capable of treating a patient presenting a torsades de pointes arrhythmic storm.

Example 2 shows that the progestogenic pills with androgenic effect can be used to prevent episodes of torsade de pointes, since they control inhibition of the IKr channel, as demonstrated by the small increase in the value of the PC1 marker. Thus, this example clearly shows a protective effect of these pills, in the presence of a joint administration of a drug which increases the risk of torsades de pointes.

Because of the properties of the progestogenic pills with androgenic effect shown in example 2 and the clinical result of example 3, the use of the progestogenic pills with androgenic effect can be envisioned, in particular in women, for the treatment of torsades de pointes, during the treatment of a patient who has just suffered an episode of torsade de pointes, or who is experiencing arrhythmic storm.

However, it is preferable to decrease the amount of estrogen in these pills, and to administer pills based on pure progestogens, as described above, in order to amplify the effect due to these molecules.

What is claimed is:

1. A method for treating torsades de pointes comprising administering to a patient a compound of general formula (I):

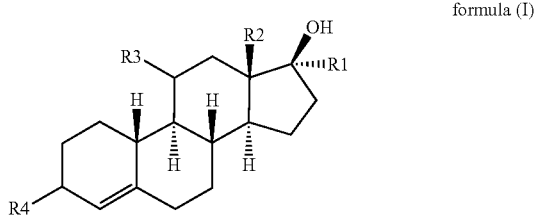

formula (I)

wherein

R1 is chosen from H, $CH_3$, $CH_2$—$CH_3$, CH=$CH_2$, and C≡CH;

R2 is chosen from $CH_3$, $CH_2$—$CH_3$, CH=$CH_2$, and C≡CH;

R3 is chosen from —H, —$CH_3$, =$CH_2$, wherein the bond between the carbon of the ring and R3 is a double bond, and ≡CH, wherein the bond between the carbon of the ring and R3 is a triple bond; and R4 is chosen from —H, —OH and =O, wherein the bond between the carbon of the ring and R4 is a double bond; wherein the compound of general formula (I) is chosen from levonorgestrel, norethisterone, desogestrel, etonogestrel, 19-nortestosterone, medroxyprogesterone, or medroxyprogesterone acetate.

2. The method of claim 1, wherein the method comprises preventing the occurrence of episodes of torsades de pointes.

3. The method of claim 1, wherein the method comprises preventing sudden death in a diabetic patient.

4. The method of claim 1, wherein the patient has a predisposition to the occurrence of torsades de pointes.

5. The method of claim 4, wherein the patient is following a treatment with a QT-increasing drug.

6. The method of claim 1, wherein the compound of general formula (I) is administered to the patient after an episode of torsade de pointes.

7. The method of claim 6, wherein the compound of general formula (I) is administered to the patient for a period of less than or equal to 15 days.

8. The method of claim 1, wherein compound of general formula (I) is administered to the patient in a daily amount between 30 pg and 3 mg.

9. The method of claim 1, wherein compound of general formula (I) is administered to the patient in a daily amount between 30 pg and 300 pg.

10. The method of claim 1, wherein compound of general formula (I) is administered orally to the patient.

11. The method of claim 1, wherein compound of general formula (I) is administered by injection to the patient.

12. The method of claim 1, wherein the patient is female.

13. The method of claim 1, further comprising administering an androgen to the patient.

14. The method of claim 13, wherein the androgen is chosen from testosterone, dehydroepiandrosterone, Δ4-androstenedione, androsterone, and dihydrotestosterone.

15. The method of claim 3, further comprising administering IGF-I to the patient.

16. The method of claim 3, further comprising administering an androgen to the patient, wherein the patient is male.

* * * * *